(12) United States Patent
Bierman (10) Patent No.: US 6,551,285 B1
(45) Date of Patent: Apr. 22, 2003

(54) MEDICAL LINE SECUREMENT DEVICE FOR USE WITH NEONATES

(75) Inventor: Steven F. Bierman, Del Mar, CA (US)

(73) Assignee: Venetec International, Inc., San Diego, CA (US)

(*) Notice: Subject to any disclaimer, the term of this patent is extended or adjusted under 35 U.S.C. 154(b) by 0 days.

(21) Appl. No.: 09/589,862

(22) Filed: Jun. 8, 2000

(51) Int. Cl.$^7$ ................................................ A61M 5/32
(52) U.S. Cl. ................................ 604/180; 128/DIG. 15
(58) Field of Search ................ 128/DIG. 15; 604/174, 604/179, 180; 24/3.1, 304, 306, DIG. 11; 248/205.2, 205.3; 224/901, 901.2

(56) References Cited

U.S. PATENT DOCUMENTS

| | | |
|---|---|---|
| 2,525,398 A | 10/1950 | Collins |
| 2,533,961 A | 12/1950 | Rousseau et al. |
| 2,707,953 A | 5/1955 | Ryan |
| 3,059,645 A | 10/1962 | Hasbrouck et al. |
| 3,167,072 A | 1/1965 | Stone et al. |
| 3,288,136 A | 11/1966 | Lund |
| 3,630,195 A | 12/1971 | Santomieri |
| 3,677,250 A | 7/1972 | Thomas |
| 3,834,380 A | 9/1974 | Boyd |
| 3,856,020 A | 12/1974 | Kovac |
| 3,906,946 A | 9/1975 | Nordstrom |
| 3,973,565 A | 8/1976 | Steer |
| 4,057,066 A | 11/1977 | Taylor |
| 4,059,105 A | 11/1977 | Cutruzzula et al. |
| 4,133,307 A | 1/1979 | Ness |
| 4,250,880 A | 2/1981 | Gordon |
| 4,316,461 A | 2/1982 | Marais et al. |
| 4,397,647 A | 8/1983 | Gordon |
| 4,449,975 A | 5/1984 | Perry |
| 4,453,933 A | 6/1984 | Speaker |
| 4,548,200 A | 10/1985 | Wapner |

(List continued on next page.)

FOREIGN PATENT DOCUMENTS

| | | |
|---|---|---|
| DE | 2341 297 A1 | 8/1973 |
| EP | 169704 A1 | 1/1986 |
| EP | 0 247 590 A2 | 12/1987 |
| GB | 2 063 679 A | 6/1981 |
| WO | WO 90/06786 | 6/1990 |
| WO | WO 92/19309 | 11/1992 |
| WO | WO 98/43691 | 10/1998 |
| WO | WO 99/16327 | 4/1999 |

OTHER PUBLICATIONS

Kendall Ltp Neonatal Supplies Brochure (1998).
Neotech Products, Inc.—Neonatal Products Brochure, 2 pages, Aug. 1998.

Primary Examiner—Sharon Kennedy
(74) Attorney, Agent, or Firm—Knobbe, Martens, Olson & Bear, LLP (57) ABSTRACT

A medical line securement device allows for inspection, repositioning, replacement and servicing of a medical line without removing an adhesive patch attached to the neonate's skin, thereby saving the thin and fragile skin of the neonate. The securement device provides a releasable attachment between the adhesive anchor patch, which is attached to the neonate, and a coupler of the securement device, which is attached to the medical line. The patch has a base, a fastening element, and an adhesive layer that attaches to the skin of a medical patient. The coupler attaches to the medical line. By this configuration, the patch and coupler cooperate to retain and releasably secure a medical line to the patient. The device is particularly adapted for use in connection with neonates and provides a small securement surface to fit onto the small body locations of a neonate. The securement device consequently can be used to couple different types of catheters or tubes at different locations on the neonates body.

48 Claims, 8 Drawing Sheets

U.S. PATENT DOCUMENTS

| | | |
|---|---|---|
| 4,633,863 A | 1/1987 | Filips et al. |
| 4,660,555 A | 4/1987 | Payton |
| 4,702,736 A | 10/1987 | Kalt et al. |
| 4,711,636 A | 12/1987 | Bierman |
| 4,726,716 A | 2/1988 | McGuire |
| 4,742,824 A | 5/1988 | Payton et al. |
| 4,821,736 A | 4/1989 | Watson |
| 4,822,342 A | 4/1989 | Brawner |
| 4,823,789 A | 4/1989 | Beisang et al. |
| 4,826,486 A | 5/1989 | Palsrok et al. |
| 4,838,878 A | 6/1989 | Kalt |
| 4,897,082 A | 1/1990 | Erskine |
| 4,898,587 A | 2/1990 | Mera |
| 4,919,654 A | 4/1990 | Kalt |
| 4,932,943 A | 6/1990 | Nowak |
| 4,955,864 A | 9/1990 | Hajduch |
| 4,976,700 A | 12/1990 | Tollini |
| 5,000,741 A | 3/1991 | Kalt |
| 5,037,397 A | 8/1991 | Kalt |
| 5,084,026 A | 1/1992 | Shapiro |
| 5,100,393 A | 3/1992 | Johnson |
| 5,147,322 A | 9/1992 | Bowen et al. |
| 5,195,981 A | 3/1993 | Johnson |
| 5,237,988 A | 8/1993 | McNeese |
| 5,266,401 A | 11/1993 | Tollini |
| 5,300,037 A | 4/1994 | Delk |
| 5,304,146 A | 4/1994 | Johnson et al. |
| 5,308,339 A | 5/1994 | Kalt et al. |
| 5,342,317 A | 8/1994 | Claywell |
| 5,370,627 A | 12/1994 | Conway |
| 5,382,239 A | 1/1995 | Orr et al. |
| 5,403,285 A | 4/1995 | Roberts |
| 5,413,562 A | 5/1995 | Swauger |
| 5,415,642 A | 5/1995 | Shepherd |
| 5,456,671 A | 10/1995 | Bierman |
| 5,496,282 A | 3/1996 | Militzer et al. |
| 5,496,283 A | 3/1996 | Alexander |
| 5,693,032 A | 12/1997 | Bierman |
| 5,755,698 A | 5/1998 | Kagan et al. |
| 5,833,663 A | 11/1998 | Bierman et al. |
| 5,916,199 A | 6/1999 | Miles |
| 5,991,979 A * | 11/1999 | Moore et al. .................. 23/306 |

* cited by examiner

MEDICAL LINE SECUREMENT DEVICE FOR USE WITH NEONATES

RELATED CASES

This application claims priority under 35 U.S.C. §119(e) from Provisional Application No. 60/______, filed Jun. 8, 1999, this provisional application being converted from application Ser. No. 09/328,047 now abandoned by petition filed on Jun. 6 2000.

BACKGROUND OF THE INVENTION

1. Field of the Invention

The present invention relates in general to a medical line securement device and, in particular, to a device that interconnects and releasably secures an elongated medical line to a neonate's skin.

2. Description of the Related Art

Premature babies usually require assistance to breathe and eat, and thus, are often fully instrumented. An endotracheal tube typically extends down the trachea of the neonate to supply oxygen to the lungs from a ventilation machine. These babies also are usually fed intravenously by an intravenous (IV) catheter inserted into a vein, usually on the dorsal side of the neonate's hand or forearm. In some cases, a naso-gastric tube may be inserted through the neonate's nose and used either for feeding/hydrating purposes or to drain gastric secretions. An arterial catheter may also be inserted on the ventral side of the neonate's hand for purposes of monitoring blood oxygenation.

The umbilical stump additionally is often catheterized. An umbilical catheter is inserted through the umbilical stump and is placed into the neonate's circulation system, with the assistance of fluoroscope or x-ray visualization, to precisely position the distal end of the catheter. The umbilical catheter allows medication to be directly introduced into the bloodstream and permits routine blood sampling, without having to frequently puncture the delicate skin of the neonate.

Each of these catheters and tubes is precisely positioned, and the position of each is fixed relative to the neonate to prevent migration or dislodgment. Healthcare personnel usually secure the IV, arterial and/or umbilical catheters using tape (and sometimes using sutures), and also fix the endotracheal and/or naso-gastric tube with tape. The catheters and tubes remain in place for several days or weeks, and often require repositioning and/or replacement on a periodic basis. The tape thus must be removed and reapplied to the neonate's delicate skin.

Tape often collects dirt and other contaminants. Normal protocol therefore also requires periodic tape changes to inhibit bacteria and germ growth at the securement site.

Frequent tape changes exfoliate the upper layers of the neonate's skin. Such exfoliation of the upper layers of skin can lead to abrasions on the neonate's skin because the neonate's skin is so thin, sensitive and fragile. Moreover, infection and disease can occur as a result of such skin wounds owing to the relatively undeveloped nature of a neonate's immune system.

Additional disadvantages exist with the use of tape to secure the catheters and tubes to the neonate. Valuable time of the healthcare provider is spent applying and reapplying the tape. Further, because most healthcare providers find such taping procedures difficult and cumbersome when wearing latex gloves, they often remove their gloves when taping. Not only does this further lengthen the taping procedure, but it also subjects the healthcare provider to possible infection. Moreover, even if the healthcare provider remains gloved, contact between the adhesive surface of the tape and the latex gloves causes micro-holes in the gloves, thereby degrading the integrity of the glove and subjecting the healthcare provider to possible infection.

A number of medical line securement devices have recently been developed that obviate the need for frequent application and removal of surgical tape and to removably secure the medical line to the patient. One such system is disclosed by U.S. Pat. No. 5,192,273 issued to the present Applicant. These systems, however, tend to be relatively large when used with neonates. A need thus exists for a medical line securement device particularly adapted for use with neonates that obviates the need for frequent application and removal of surgical tape.

SUMMARY OF THE INVENTION

The medical line securement device of the present invention is particularly adapted for use with neonates and obviates the need for frequent application and removal of surgical tape. The device provides a small securement surface to accommodate the small body parts of a neonate, through which the device releasably engages the medical line to the neonate's skin.

The medical line securement device of the present invention also recognizes the need for a multifunctioning device that can secure a variety of medical lines (e.g., catheters and tubes) to a variety of locations on the neonate's body. One way that the securement device fulfils this need is by the components of the securement device being configured to cooperate with each other in multiple orientations. The securement device can also be part of a kit that includes a plurality of components, each of which has one of a variety of sizes, shapes and adhesives. Particular components can be selected based on the particular medical line used and the particular portion of the neonate's skin to which the medical line will be attached.

In accordance with one aspect of the present invention, a securement device is provided for securing a medical line to the skin of a patient. The securement device comprises a patch including at least one fastener element on a first side of the patch and an adhesive on at least a portion of an opposite second side of the patch to secure the patch to the skin of the patient. A coupler is releasably attachable to the patch. The coupler includes a patch attachment section and a medical line attachment section connected together. Both sections include a first side and an opposite second side. At least two fastener elements are disposed on the patch attachment section of the coupler. Each is cooperative with the fastener element on the patch to releasably secure the coupler to the patch. One is positioned on the first side of the patch attachment section and the other is positioned on the second side of the patch attachment section. An adhesive is disposed on the first side of the medical line attachment section. The resulting two-sided patch attachment section permits the coupler to be attached to the patch regardless of the orientation of the adhesive side of the medical line attachment section.

In a preferred mode, the patch is configured and sized so that the fastener element covers only a portion of the first side of the patch. The remainder of the patch is thereby configured so that it can be trimmed into a shape which matches the shape of the region of the skin of the patient to which it will be applied. In this manner, it is possible for a medical practitioner to custom shape the adhesive surface of the patch so as to provide securement to the skin of the patient, while minimizing the unusable surface are of the patch which may irritate the patient, or complicate attachment of the patch.

Another aspect of the present invention involves a securement device comprising a patch including at least one fastener element on a first side of the patch and an adhesive on at least a portion of an opposite second side of the patch to secure the patch to the skin of the patient. A coupler has a patch attachment section and a medical line attachment section which are connected together by a narrow flexible neck. The patch attachment section includes at least one fastener element that is cooperative with the fastener element on the patch to releasably secure the coupler to the patch. An adhesive on the medical line attachment section is capable of attaching the coupler to the medical line to be secured to the patient. The flexible neck permits the medical line attachment section to assume different orientations relative to the patch attachment section when attached to the patch.

Another aspect of the present invention involves including within a kit for securing a medical line to the skin of a patient a number of parts including at least one patch for attachment to the skin of a patient, at least one coupler for attachment to the medical line and releasable connection to the patch, and at least one tape strip for any additional securement. Such a kit may include multiple patches of different sizes and configurations, as well as using different types of adhesive. Multiple couplers appropriate to securing different types of lines may also be included within such a kit.

Further aspects, features and advantages of the present invention will become apparent from the detailed description of the preferred embodiments that follow.

BRIEF DESCRIPTION OF THE DRAWINGS

The above-mentioned and other features of the invention will now be described with reference to the drawings of a preferred embodiment which is intended to illustrate but not to limit the invention. The drawings contain the following figures.

DETAILED DESCRIPTION OF THE PREFERRED EMBODIMENT

The illustrated embodiment of the medical line securement device 10 is disclosed in the context of use with an exemplary medical infusion line 12. The infusion line 12 comprises an intravenous (IV) supply tube 14 coupled to a hub 18 of an indwelling IV catheter 16. The principles of the present invention, however, are not limited to IV catheters and lines. Instead, it will be understood by one of skill in the art, in view of the present disclosure, that the securement device disclosed herein can also be used with other types of medical lines, such as with other catheters, fluid drainage and delivery tubes, electrical leads and the like. It is also understood that the skilled artisan can readily adapt the securement device for use in other applications to retain many different types of medical lines to a patient. Thus, the illustration and description of the medical line securement device in connection with an IV line (e.g., the supply line 14 and the IV catheter 16) is merely exemplary of one possible application of the securement device.

The securement device 10 has particular applicability in connection with securing a medical line to a neonate. The device can be configured to provide a small securement surface to fit onto the small body of the neonate. The device, however, can also be successfully utilized with any medical patient, notwithstanding the size or age of the patient, although the size of the device might have to increase. Thus, the illustration and description of the securement device in context of use with a neonate is merely exemplary of one possible application of the securement device.

The medical line securement device 10 provides for secure attachment of the medical line to the neonate's skin without the use of surgical tape. Thus, if a segment of the medical line is periodically repositioned or replaced, a component of the securement device attached to the neonate's skin can remain in place while another component of the securement device is simply and quickly disengaged to release the medical line from the securement device. Similarly, the disengaged component of the securement device can be easily engaged or reengaged to secure or resecure the medical line to the neonate. Thus, the securement device need not be applied to and removed from the neonate's skin on multiple occasions. Moreover, the component of the securement device, which is attached to the medical line, can be easily attached to or replaced on the medical line.

Figure 1:
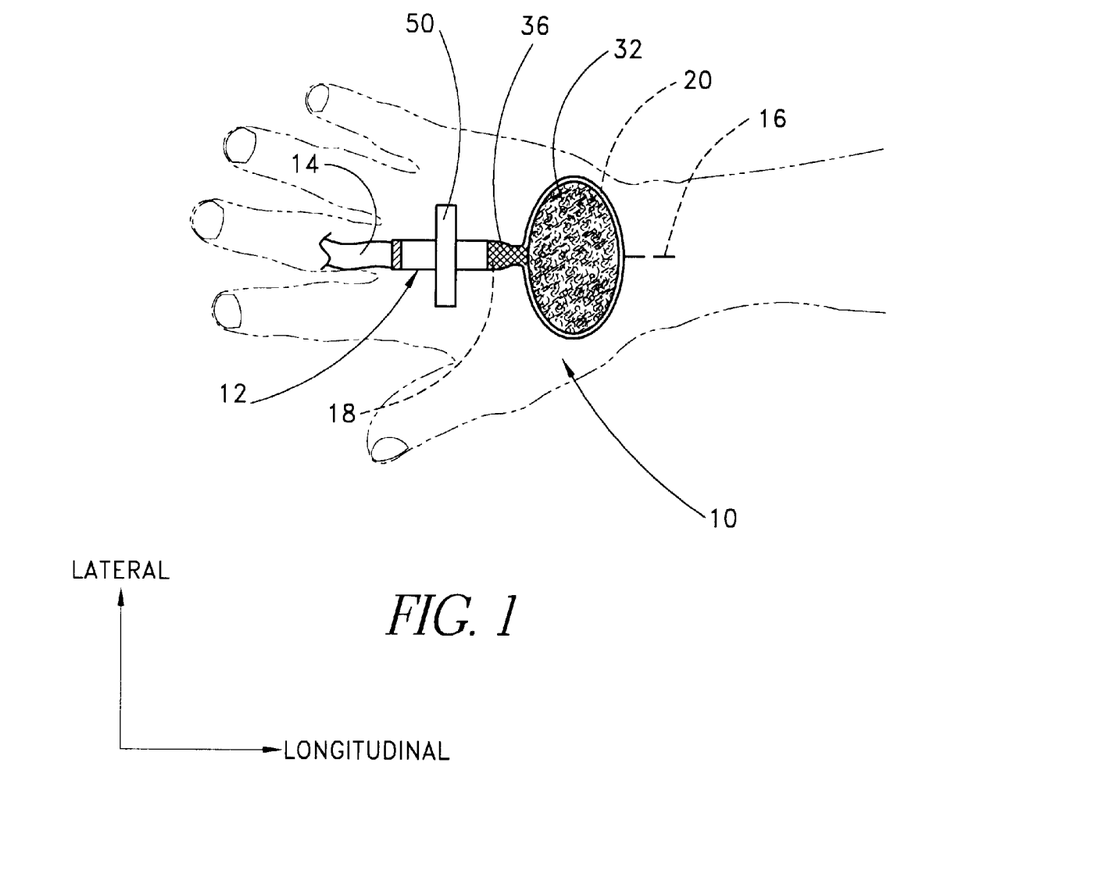
FIG. 1 is a top plan view of a medical line securement device configured in accordance with a preferred embodiment of the present invention, and illustrating an exemplary use of the device mounted on the dorsal side of a neonate's hand.
Figure 11:
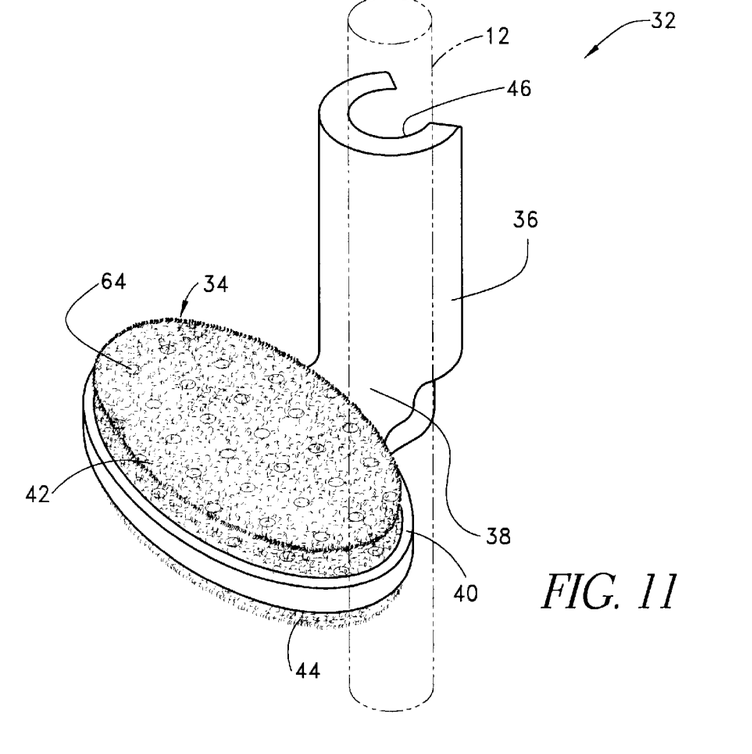
FIG. 11 is a perspective view of the coupler of FIG. 10 as attached to a medical line (e.g., an umbilical catheter), which is shown in phantom.

As will be apparent from the description below, the present securement device 10 can be used with a variety of different catheters and tubes. Although FIG. 1 illustrates the securement device 10 located on the dorsal side of a neonate's hand (illustrated in phantom lines), the present invention also may be used at other locations on the neonate's body, as described below. For instance, the securement device may be used on the neonate's face to secure an endotracheal tube (FIG. 8) or a naso-gastric tube (as illustrated in phantom in FIG. 8). The securement device 10 may also be used on the neonate's abdomen to secure an umbilical catheter that is inserted into the umbilical stump of a neonate (FIGS. 9 and 11).

To assist in the description of these components of the securement device 10, the following coordinate terms are used. A "longitudinal axis" is generally parallel to the section of the medical line secured by the securement device 10. A "lateral axis" is normal to the longitudinal axis and is generally parallel to the plane of the minor axis of a patch 20 illustrated in FIG. 1. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. A detailed description of the securement device 10 and associated methods of use now follow.

With reference to FIG. 1, the medical line securement device 10 principally comprises a patch 20 and a coupler 32. The patch 20 has a base 22 and an adhesive 24 that attaches to the skin of the neonate when used. The base 22 supports at least one fastener element 26, preferably a VELCRO® hook fastener element. The coupler 32 also has a base layer 40 and an adhesive 46 that attaches the base layer 40 to the medical line 12. The base layer 40 also supports at least one fastener element 42, preferably a VELCRO® loop fastener element, that releasably attaches to the fastener element 26 of the patch 20. By this configuration, the patch 20 and the coupler 32 cooperate to releasably secure a medical line 12 to the neonate.

Patch

Figure 2:
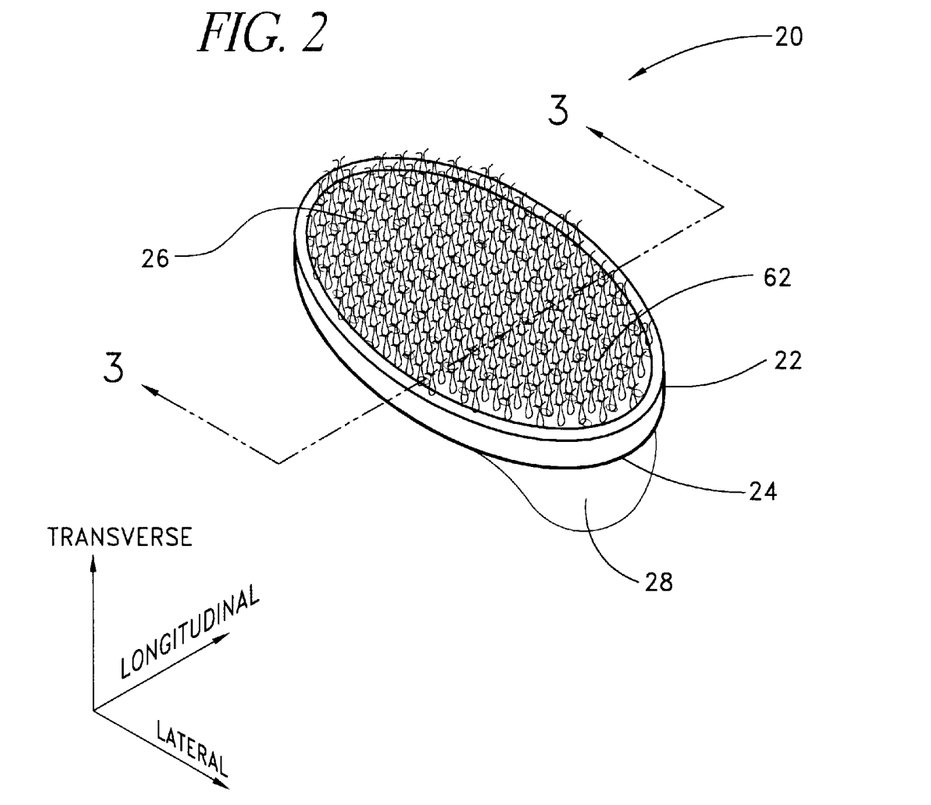
FIG. 2 is a perspective view of a patch of the securement device of FIG. 1.
Figure 3:
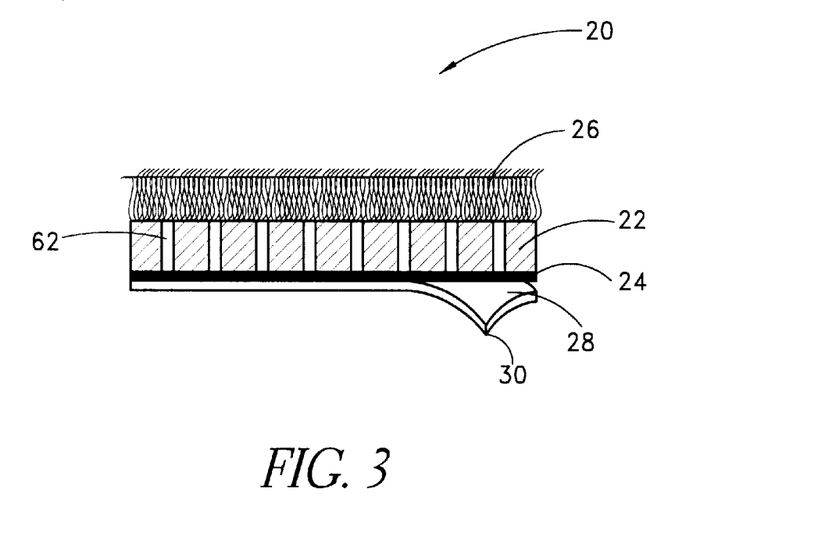
FIG. 3 is a side elevational view of the patch of FIG. 2.

FIGS. 2 and 3 illustrate the patch 20 that is attachable to the neonate's skin to anchor the device to the child. The patch 20 desirably has a shape suited for the particular use of the securement device 10. For instance, in the illustrated embodiment, the patch 20 has an elongated oval shape that allows the patch 20 to be located close to an insertion site of a catheter or tube into the neonate while providing a large surface area to ensure good adhesion to the child's skin. As described in greater detail below, a preferred mode of securement device 10 desirably can be used with several types of medical lines (e.g., catheters and tubes) at various locations on the patient's body. The elongated oval shape permits the patch 20 to fit on both confined areas (e.g., on the child's chin) and larger areas (e.g., on the child's abdomen) on the patient. The patch 20, however, can be configured in any of a variety of shapes, such as rectangular, square, circular, oblong, linear, curved, curvilinear and the like, and can include reliefs, recesses or openings to surround or partially surround the anchored medical line.

In the illustrated oval embodiment, the oval shape of the patch 20 has a major axis length of about 25 mm and a minor axis length of about 15 mm. This size provides sufficient adhesion while fitting onto confined areas on the neonate (e.g., the child's chin). The patch 20, however, can have a variety of other sizes for applications at other locations on the body and for larger patients (e.g., adults).

The patch 20 has a low-profile configuration and, in one preferred mode, is generally flexible. In the illustrated embodiment, the patch 20 has generally a planar configuration that is flexible along both its major and minor axes. The generally flexible nature of the patch 20 permits the patch 20 to conform to a surface curvature at various locations on the patient's body (e.g., the surface curvature of the neonate's chin, nose or forearm).

In some applications, the patch 20 can be rigid so as to maintain a particular shape. For example, a patch 20 can have a curved profile when designed for use on a generally curved portion of skin (e.g., a chin). The curved profile advantageously could have a curvature that generally matches the curvature of the skin where the patch 20 is to be positioned.

As understood from FIGS. 2 and 3, the patch 20 principally comprises a base 22, an adhesive 24 and at least one fastener element 26. The adhesive is disposed on one side of the base while the fastener element 26 is disposed on the opposite side of the base. Although not included in the illustrated embodiment, one or more layers (not shown) can be arranged between the base 22 and adhesive 24 and/or between the base 22 and the fastener element 26 for a variety of particular purposes. For example, a stiffening layer can be used to provide rigidity to the patch 20, a cushioning layer can be used to pad the patch 20 and protect the skin located under the patch 20, and/or a strengthening layer can be used to increase the tensile or shear strength of the patch 20.

In the illustrated embodiment, the fastener element 26 comprises a plurality of hooks of a hook-and-loop fastening system (e.g., VELCRO®). In one mode, the base and fastener element are integrally formed. An exemplary material for the base and hook fastener element that has been found suitable is commercially available from Velcro USA, Manchester, N.H., as part number HTH 811. A variety of other hook fasteners may be used to perform the intended function of fastening the patch 20 to the coupler 32. Moreover, any of a variety of fastening members that provide for releasable securement of the medical line to the neonate's skin, such as adhesives, barbs, clips, and other structures can be used between the patch 20 and the coupler 32. A hook-and-loop fastener though offers ease of application (i.e., little pressure applied to the neonate when engaging and disengaging the loops from the hooks), long life and repeatability of use, minimal abrasiveness, and low cost.

The adhesive 24 is disposed on a side of the base 22 to be attached to the neonate's skin and covers a sufficient portion of the base 22 to provide adequate adhesion to hold the patch 20 to the skin and to inhibit unintentional detachment. In a preferred mode, the adhesive 24 forms a layer that covers the entire bottom surface of the base 22; however, the adhesive 24 can be applied in a particular pattern (e.g., around the periphery) to provide good adhesion but reduce the amount of skin exfoliation when the patch 20 is removed.

A variety of suitable adhesives can be used. The particular one selected desirably accounts for the area of the body on which the patch 20 is to be placed and the delicacy of the skin at that location and of the particular patient (e.g., a neonate). For example, a hydrocolloid or hydrogel adhesive offer good adhesion and are skin gentle; hydrogels, however, are fluid dissolvable and possibly should not be used in areas where fluids are often present (e.g., about the mouth, such as with an endotracheal tube). A suitable adhesive layer can be formed with a single coated polyurethane with 0.018 inch (0.46 mm) of hydrocolloid adhesive, available commercially from Avery Dennison, Special Tape Division, Painesville, Ohio, Part Number MED-5580H. A polyethylene embossed tape, such as Transpore™ surgical tape, available commercially from Minnesota Mining & Manufacturing, Corp. (3M), Minneapolis, Minn., Part No. 1527-L, can also be used to form the adhesive layer for use with neonates. Transpore™ tape offers slightly better adhesion over a hydrocolloid adhesive, but is not as gentle on skin when removed. Another suitable adhesive is an acrylic adhesive that may be applied via a transfer tape (available commercially from 3M as Part No. 9272LE) or that may come applied to the molded hook base of the hook-and-loop fastener (available commercially from 3M as Part No. SJ-3516).

The patch 20 desirably is moisture-vapor permeable for use in at least some applications. In the illustrated embodiment, the base 22 has a plurality of holes 62 and the adhesive layer 24 is formed of a breathable material, such as a hydrocolloid adhesive. Use of holes and breathable material allows air to be in exchange with the portion of the neonate's skin that is covered by the securement device 10 and to inhibit moisture-vapor from being trapped against the skin. Moisture-vapor exchange is useful in inhibiting bacterial and fungal growth as well as in accelerating healing. (A variety of other structures of course could be used with the base 22 instead of holes, such as slots, perforations, and thinning the base 22 so that air and moisture-vapor can pass therethrough.) Also, the adhesive layer can also be patterned so as to provide a plurality of holes, slots, openings and the like to allow or further air flow through the patch 20. In a variety of applications, though, the patch 20 need not be moisture-vapor permeable, i.e., need not include such holes and breathable adhesive.

As seen in FIG. 3, a removable backing or release liner 28 desirably covers the adhesive layer 24 before use. The liner 28 can be paper, plastic or any other suitable material well known to those of ordinary skill in the art. The liner 28 preferably resists tearing and may be unitary, as illustrated, or divided into a plurality of pieces to ease removal of the liner from the adhesive and to ease attachment of the patch 20 onto the neonate's skin (similar to the tape strips illustrated in FIGS. 6 and 7). The liner 28 may also advantageously extend beyond at least one edge of the adhesive layer 24 to ease removal of the liner from the adhesive layer 24. If the liner 28 is divided into a plurality of pieces, the pieces are desirably split near a center line of the patch 20 in order to expose only half of the adhesive layer 24 at one time. One or more tabs 30 may also be folded over, or back onto the liner 28. The tab 30 overcomes any need for the healthcare provider to pick at a corner edge or other segment of the liner 28 in order to separate the liner 28 from the adhesive layer 24. The liner 28 may also include indicia in the form of dots, words, figures or the like to indicate the placement of fingers when removing the liner 28 from the patch 20.

Coupler

Figure 4:
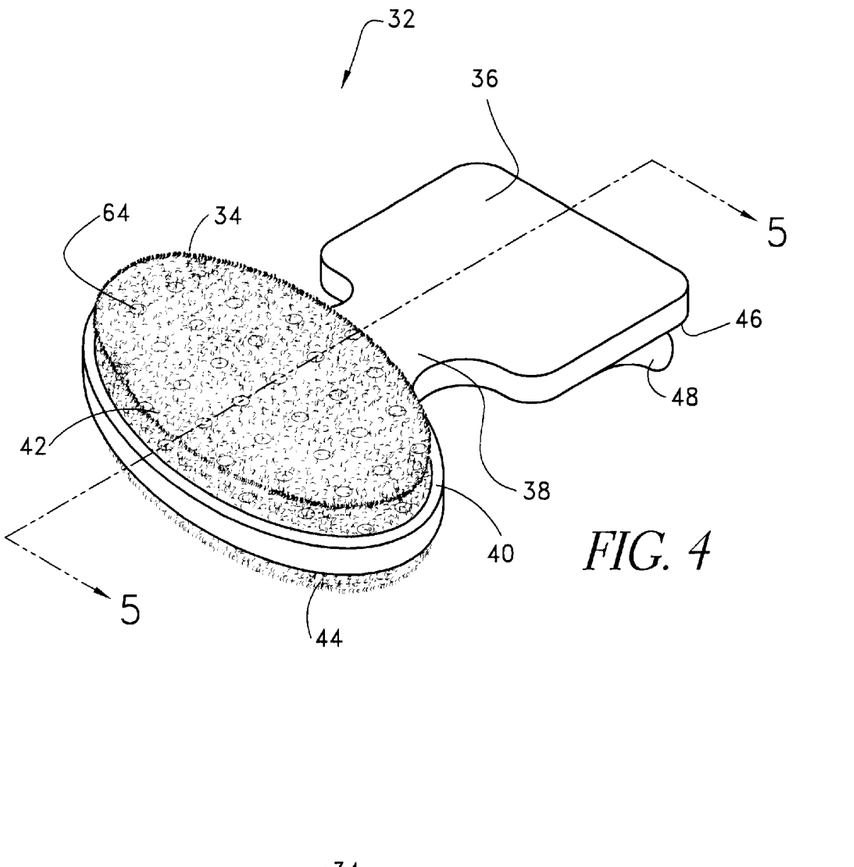
FIG. 4 is a perspective view of a coupler of the securement device of FIG. 1.
Figure 5:
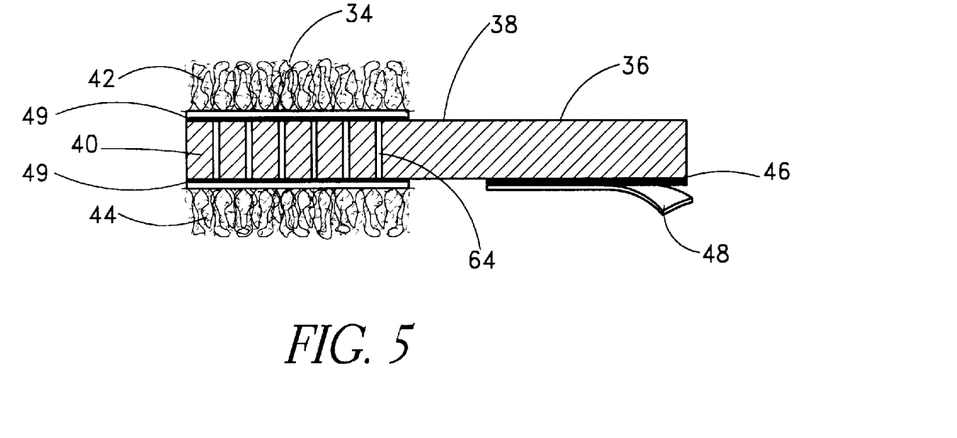
FIG. 5 is a side elevational view of the coupler of FIG. 4.

FIGS. 4 and 5 best illustrate the coupler 32 which couples the medical line 12 to the patch 20. The coupler 32 has a patch attachment section 34 and a medical line attachment section 36. In one preferred mode, a flexible neck 38 couples the patch attachment section 34 to the medical line attachment section 36.

The patch attachment section 34 cooperates with the patch 20 such that the coupler 32 is releasably attachable to the patch 20 at this section. The patch attachment section 34 desirably is coextensive or slightly overlapping with the size and shape of the patch 20 (i.e., desirably has the same or greater geometric configuration as the patch). The patch attachment section 34, however, need not have the same geometric configuration as the patch 20. For instance, the patch attachment section 34 can be sized to extend beyond any of the longitudinal, lateral, or transverse edges of the patch 20.

The patch attachment section 34 includes at least one fastener element 42 that cooperates with the fastener element 26 of the patch 20. In the illustrated variation of the coupler, the patch attachment section 34 includes at least two like fastener elements 42, 44; one fastener element 42 is positioned on one side of the patch attachment section 34 and the other fastener element 44 is positioned on an opposite side of the patch attachment section 34. The presence of fastener elements 42, 44 on the opposite sides of the patch attachment section 34 permits either side of the section to be attached to the patch 20, as discussed in detail below. While a variety of fastener elements can be used with the coupler, the fastener elements desirably are non-abrasive for use with neonates.

In the illustrated embodiment, each fastener element 42, 44 comprises a plurality of loops that form a loop portion of the hook-and-loop fastener. The loops extend from woven or molded base and form a soft, non-abrasive, felt-like matting. An exemplary type of loop fastener element that has been found suitable is commercially available from Velcro, USA as part number HTH 3610. Of course, where the patch 20 includes another type of fastener element, the patch attachment section 34 of the coupler 20 should include corresponding fastener elements that each cooperate with the fastener element on the patch 20.

The loop fastener elements 42, 44 on the patch attachment section 34 desirably have the same size and configuration, but need not have. The resulting double-sided fastener elements assist in the multi-functionality of the securement device 10, as described below.

The medical line attachment section 36 interconnects the medical line 12 (or a hub or fitting 18 of a medical line 12) with the coupler 32. The medical line attachment section 36 can be configured in a wide variety of sizes and shapes. In the illustrated embodiment, the medical line attachment section 36 has a planar shape that can be placed on and preferably wrapped around at least a portion of the medical line 12. For this reason, the medical line attachment section 36 desirably has a sufficient size to provide adequate contact with the medical line 12 to ensure a good coupling. In one form, as illustrated in FIGS. 4 and 5, the medical line attachment section 36 has a generally rectangular or square shape with a longitudinal length sufficient to inhibit separation of the medical line 12 from the patch 20. In a preferred form, the longitudinal length is about 5–30 mm and more preferably about 12 mm. Also, the medical line attachment section 36 has a lateral width sufficient to inhibit separation of the medical line 12 from the patch 20. In a preferred form, the lateral width of the medical line attachment section 36 is about 5–30 mm and more preferably about 14 mm. Other sizes and shapes of the medical line attachment section 36 of course are also possible in order to suit a specific application of the securement device 10.

An adhesive 46 is disposed on at least a portion of at least one side of the medical line attachment section 36 to adhere the medical line 12 to the coupler 32. In a preferred mode, the adhesive 46 forms a layer that covers the entire surface of the medical line attachment section 36; however, the adhesive can be applied in a particular pattern (e.g., around the periphery). In addition, both sides of the medical line attachment section 36 can include adhesive so as either to further the bi-directional aspect of the coupler 32, or to give the coupler 32 the bi-directional aspect if the coupler includes a fastener element 42 only on one side of the patch attachment section 34.

A variety of suitable adhesives can be used. One such suitable adhesive is 300LSE Acrylic, which is commercially available from the 3M Company as part number 9672LE5. A removable paper backing or plastic release liner 48 desirably covers the adhesive layer 46 before use and is similar to that described in connection with the liner 28 of the patch 20. In another variation where both sides of the medical line attachment section 36 include adhesive, a dedicated release liner 48 covers the adhesive on each side of the coupler 32.

The neck or bridge 38 of the coupler 32 interconnects the patch attachment section 34 and the medical line attachment section 36 to provide a flexible coupling therebetween. The neck 38 is desirably substantially inelastic and flexible, with a sufficiently narrow transverse width and sufficiently long transverse length to allow the neck 38 to bend and twist. In this manner, the neck 38 can twist and bend relative to the patch attachment section 34 and the medical line attachment section 36 to allow the patch attachment station 34 and the medical line attachment station 36 to have differing orientations with respect to each other, yet still be attached through the flexible neck 38.

The neck is comprised of, at least in part, a material resistant to failure due to longitudinal loading exerted by the medical line. The tensile strength of the material in the longitudinal direction desirably is greater than about 15 lbs./inch, more desirably greater than about 25 lbs./inch, and most desirably greater than about 40 lbs./inch.

At the same time, the material is flexible with a relative low modulus of rigidity (as compared to at least the patch attachment section 34), such that deflections of the neck 38 during normal use on a patient do not cause substantial internal stresses within the coupler 32. Substantial internal stress is that amount of force that causes the medical line attachment section 36 to lift from a portion of the medical line 12 to which it is attached. It has been determined that materials having a modulus of elasticity of less than about 500,000 p.s.i. do not cause substantial internal stress. For purposes of the present description, such materials are considered substantially inelastic. The flexible material desirably has a modulus of elasticity of less than about 200,000 p.s.i., more desirably less than about 150,000 p.s.i., and particularly less than about 100,000 p.s.i.

The neck 38 also advantageously exhibits a shear strength sufficient to withstand tearing in the context of its intended use. Desirably, the shear strength of the neck 38, measured in a propagating or Elmendorff tear, is at least about 0.5 lb./inch, more desirably greater than about 0.8 lb./inch, and particularly greater than about 1.2 lbs./inch.

Materials that have been found suitable for a neck materials include polyethylenes, and particularly high density polyethylenes. This neck 38 of the illustrated embodiment comprises a spun bonded olefin, paper-like material available from E.I. du Pont de Nemours, Inc. under the trade name Tyvek™. "Merge 18024" is a specific type of Tyvek™ which is particularly advantageous for use in the medical field and is available in a nominal thickness of 0.0073 inch (0.19 mm). It is understood, however, that the neck 38 can also be made from other types of materials.

In the exemplary embodiment, the flexible neck 38 has a generally narrowed midsection with a longitudinal length of about 2–20 mm and desirably about 3–5 mm. The neck 38 can have any of a variety of shapes, such as rectangular. The transverse width of the flexible neck 38 is about one third the transverse width of the patch attachment section 34 at its narrowest section; however, this width can vary widely depending on the amount of flexibility or strength required of the neck 38. In general, the wider the neck is, the more strength the neck has, and the narrower the neck is, the more flexibility the neck has.

In the illustrated embodiment, a unitary base layer 40 forms at least a portion of the neck 38, the patch attachment section 34 and the medical line attachment section 36. The loop fastener elements 42, 44 are attached to opposing sides of the base layer 40 at the patch attachment section 34. A suitable adhesive 49 (e.g., an acrylic adhesive) secures the loop fastener elements 42, 44 to the base layer 40. Likewise, in the illustrated embodiment, the acrylic adhesive layer 46 is disposed on one side of the base layer 40 at the medical line attachment section 36. A base layer 40 thus desirably extends the longitudinal length of the coupler 32 and supports the components of the coupler 32.

The base layer 40 can be manufactured from a variety of materials. One such suitable material, as noted above, is commercially available from I.E. DuPont de Nemours, Inc., under the trade name Tyvek™. Such material not only provides the desired strength and flexibility to the neck 38, but also permits the medical line attachment section 36 to be wrapped around the medical line 12 without substantial internal stress.

In another form, a different material can be used as the base layer 40 with a strengthening spine (not shown) extending at least between the medical line attachment section 36 and the patch attachment section 34. This type of construction is illustrated in U.S. Pat. No. 5,833,663, entitled Naso-Gastric Tube Retainer, filed in the names of Steven F. Bierman and Gregory M. Weiss, and assigned to the assignee hereof. The disclosure of U.S. Pat. No. 5,833,663 is hereby incorporated by reference.

In those devices constructed to inhibit moisture-vapor from being trapped beneath the securement device 10, the coupler 32 can be configured to also include breathing openings 64 to further air and moisture-vapor exchange across the coupler 32; however, it is understood that the securement device 10 can still permit moisture-vapor passage through the patch 20 even with the absence of such openings 64 in the coupler 32 due to the permeable nature of the loop fastener elements 42, 44.

As illustrated in FIGS. 4 and 5, the section of the base layer 40, which forms a portion of the patch attachment section 34 of the coupler 32, includes a plurality of openings 64. The openings 64 permit air to be in exchange with the portion of the neonate's skin that is covered by the securement device 10.

The coupler 32 and the patch 20 are both desirably formed by a conversion process. The layers of the coupler 32 and of the patch 20 are assembled together through conversion rollers and the corresponding components (i.e., the coupler 32 or the patch 20) are die cut on a rotary die in accordance with known manufacturing methods. The perforation holes 62, 64 in the patch 20 and the coupler 34 can also be formed through the converter process.

Trimmable Patch Design

Another embodiment of the present securement device makes use of the coupler 32 as described above used with a patch 120 as shown in FIGS. 7A and 7B. This patch design is substantially similar to the patch 20 of FIGS. 2 and 3 in construction and materials. However, this design is intended to be trimmed into an appropriate shape prior to application to the patient, as is described below.

The patch 120 desirably has a shape which may be larger than is necessary in some applications to provide sufficient adhesion to the skin of the patient. For instance, in the illustrated embodiment of FIGS. 7A and 7B, the patch 120 has a substantially rectangular planform shape which is larger than that of the patch 20 as shown in FIG. 2. This larger planform will allow a nurse or other medical practitioner to cut the patch down to the desired shape before application to the skin of a patient.

Figure 7:
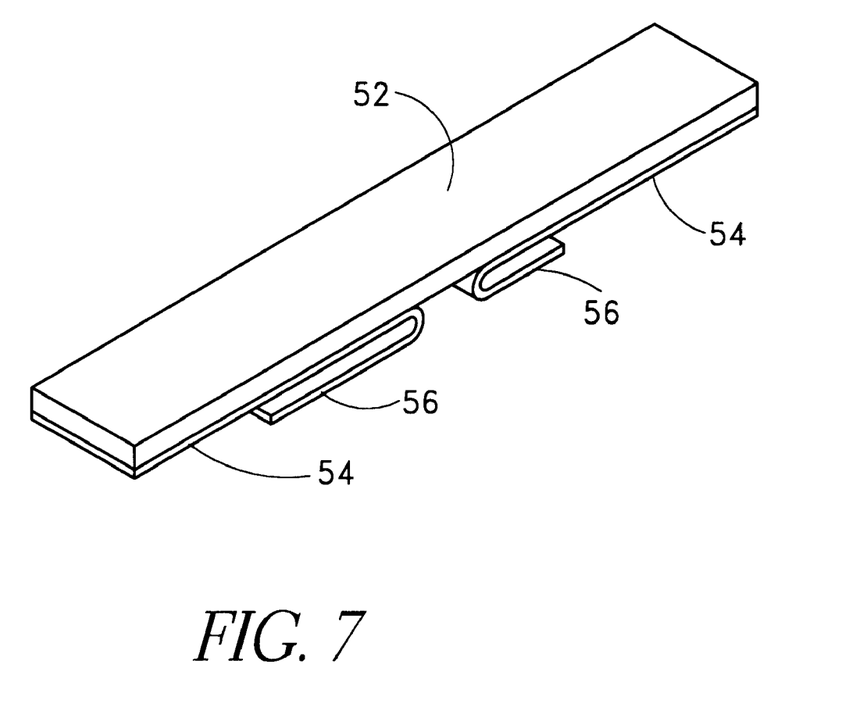
FIG. 7 is a side elevational view of the tape of FIG. 6.
Figure 7A:
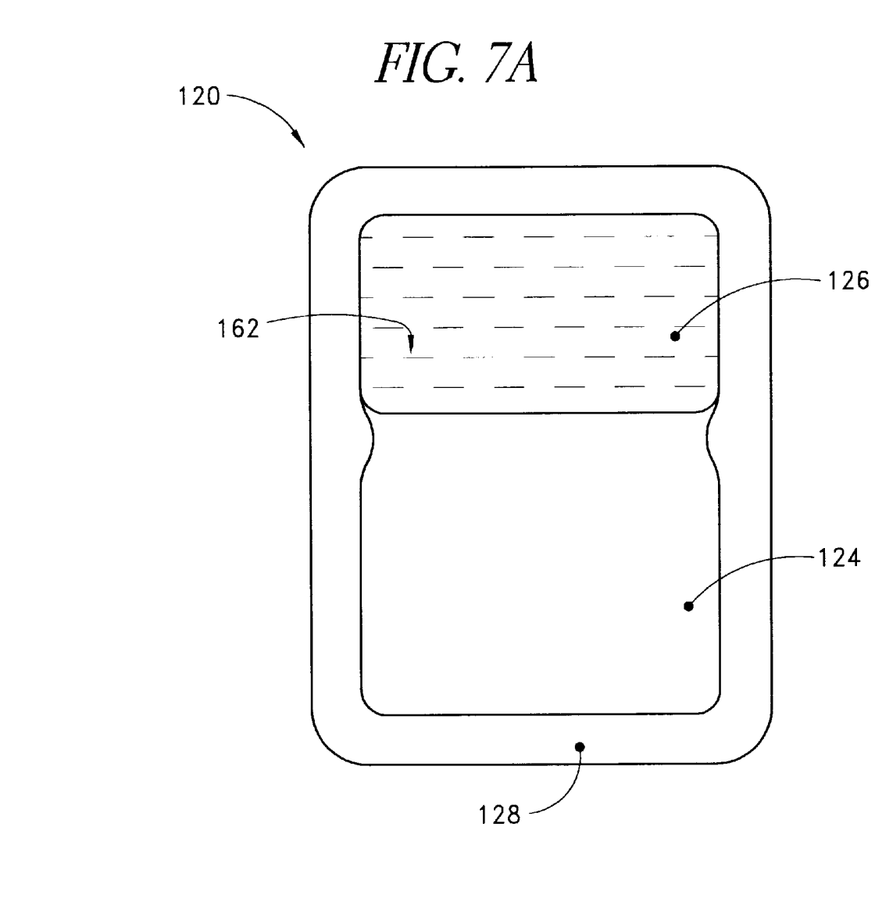
FIG. 7A is a top plan view of another patch design for use with the coupler of FIG. 4.
Figure 7B:
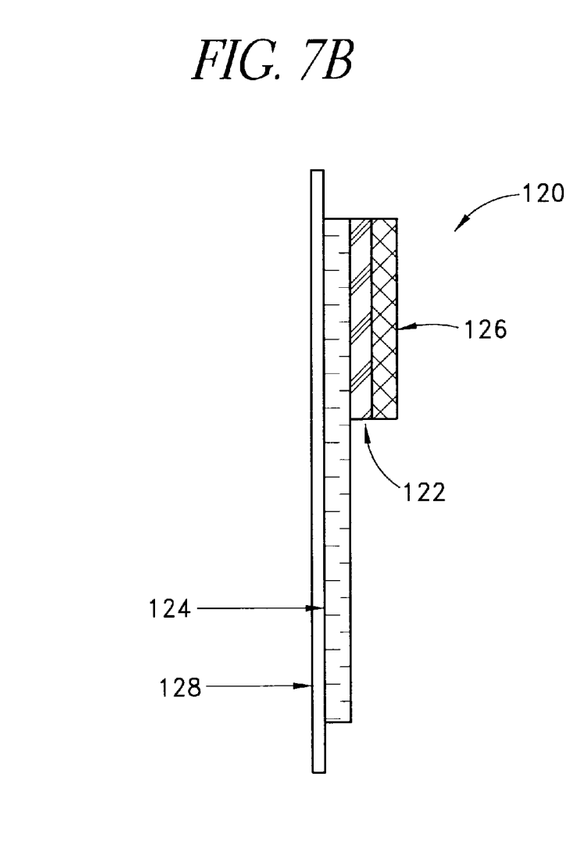
FIG. 7B is a side elevational view of the patch of FIG. 7A.

Because the patch may be cut down from its initial size, it is advantageous for the patch 120 to be sized larger than necessary for some applications (e.g., for securement of an endo-tracheal tube) to provide sufficient adhesion to the patient, since the patch may be cut down to a size smaller than its original dimension before use. In use in other applications (e.g., for securement of an umbilical catheter), the patch can be adherered to the neonate without trimming the patch. This larger size furthers the securement provided by the securement device. Although the illustrated embodiment is rectangular, the patch 120 can be configured in any of a variety of shapes, such as square, circular, oblong, or curved, and can include reliefs, recesses or openings to surround or partially surround the anchored medical line.

In an exemplifying mode, the patch 120 preferably has a longitudinal dimension of about 30 to 45 mm and a lateral dimension of about 20 to 35 mm. This size provides adequate surface area for an appropriately sized and shaped adhesive anchor to be formed by a medical practitioner by cutting the patch into a desired shape for the specific patient to be treated. The patch can have a variety of other sizes, however, for applications involving larger patients.

The patch comprises a base 122, an adhesive 124, and at least one fastener element 126. The adhesive 124 is disposed on one side of the base while the fastener elements 126 is disposed on the opposite side of the base. As in the previous embodiments, additional layers (not shown) may be arranged between the base 122 and adhesive 124 and/or between the base 122 and the fastener element 126 for a variety of particular purposes.

As in the previous embodiment, the patch 120 may be constructed including perforations 162 or other openings which allow for the patch to be moisture permeable so as to be more gentle to the skin of the patient.

The fastener element 126 may advantageously comprise the hook portion of a hook-and-loop fastener system, as described above. This fastener element 126 is sized to only cover a portion of the underlying adhesive 124 substrate. The remainder of the surface area of the patch consists of only the adhesive substrate 124 without any fastener element. This portion of the patch is suitable for being trimmed into an appropriate shape for the particular patient by a medical practitioner immediately prior to application to the patient. In a preferred mode, the patch may be trimmed using sterile scissors, however, other instruments may be used as appropriate to the application to which the device is being put.

In order to facilitate this cutting of the patch, the adhesive substrate 124 is preferably constructed using a fairly thin material, such as polyurethane film, upon one side of which the adhesive surface is applied. As in the prior embodiment, the adhesive is desirably covered by a release liner 128 which is used to protect the adhesive surface during shipping and cutting of the patch 120. The liner 128 is removed prior to application to the patient so as to expose the adhesive 124.

Additional perforations or other scoring of the patch 120 may also be included in order to provide lines along which the patch may be torn so as to alter the configuration of the patch prior to application by the medical practitioner. In this way, patches may be provided which may be customized in size and configuration to the particular application without the use of additional instruments such as scissors.

By trimming the patch 120 into a shape which is most appropriate to the portion of the patient to which the patch will be applied, a better fit upon the patient may be achieved. For instance, for use with a naso-tracheal tube, the patch 120 may be trimmed to attach to the forehead and bridge of the nose of the neonate, but not cover the eyes of the patient. When used on the hand of a neonate, the patch may be trimmed into a shape that matches the shape of the dorsal surface of the hand of the neonate. In this way, a more secure attachment to the patient is obtained with a minimum of unused adhesive surface (i.e., adhesive surfaces which cannot make a secure contact with the skin of the patient).

The surface area of the patch 120 which is not covered by the fastener element 126 may provide an additional benefit for the practitioner in that counter-pressure may be applied to this surface while the coupler 32 is disengaged from the patch. This pressure prevents inadvertent stress upon the patch which might dislodge the patch from the skin of the patient during removal of the coupler.

Medical Line Securement Kit

The above described securement devices can be included as part of a medical line securement kit. For example, a securement kit can include a plurality of patches with different types of adhesive layers. One patch may include a hypoallergenic adhesive (e.g.; hydrocolloid), and another patch may include a medical grade adhesive (e.g., Transpore™). The kit can also include several couplers for securement of a medical line at multiple locations, for securement of several medical lines, or for replacement purposes. In some applications, the kit can include patches and couplers in more than one size (e.g., in a range of sizes) or shape (e.g., both an oval patch, and a larger rectangular patch for trimming).

Figure 6:
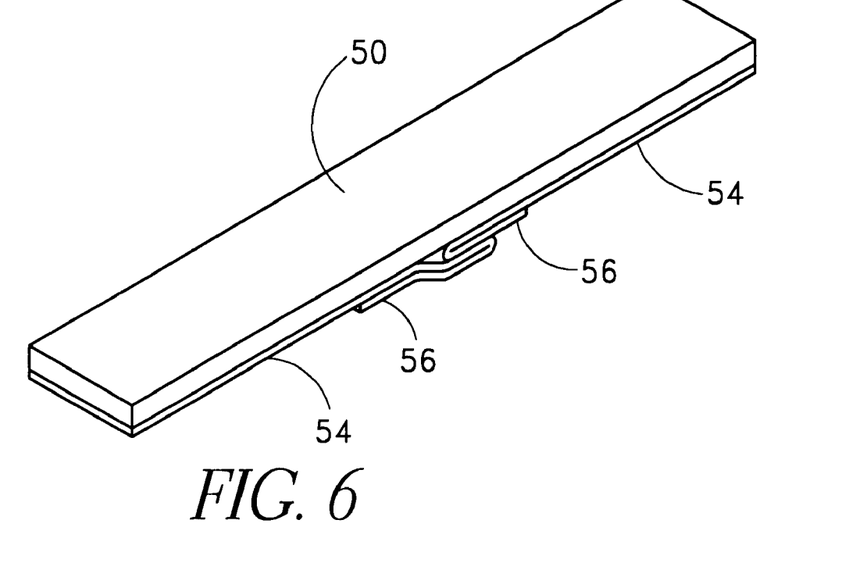
FIG. 6 is a perspective view of an elongated piece of tape which can be used with the securement device of FIG. 1.

The kit also includes at least one, and possibly a plurality of tape strips. The tape strips can also include different types of adhesive layers. FIGS. 6 and 7 illustrate two tape strips 50, 52 contained within the kit. One of the tape strips 50 is a latex based tape available commercially as Hy-Tape (commonly referred to as "pink tape") from Hy-Tape Corporation of Yonkers, N.Y. Another tape strip 52 can be a strip of Transpore™ tape available commercially from 3M Corporation. Each of the tape strips 50, 52 includes an adhesive layer initially covered by a release liner 54. The liner 54 can include pull tabs 56, as illustrated in FIGS. 6 and 7.

Exemplary Uses of the Device

The securement device 10 allows a healthcare provider to secure the medical line 12 to the neonate's skin. The securement device 10 can be secured to a variety of locations on the neonate, such as, for example, to the neonate's abdomen (to secure an umbilical catheter inserted through the neonate's umbilical stump), to the neonate's chin or nose (to secure an endotracheal tube or naso-gastric tube, respectively), to the neonate's wrist or forearm (to secure an indwelling IV or arterial catheter), and to other locations on the neonate's body in proximity to the insertion site of a medical line 12. The securement device 10 can also be used simply to hold a medical line (e.g., electrical lead) to the patient's body.

FIG. 1 illustrates the securement device 10 attached to a catheter hub 18 of an indwelling IV catheter 16 to secure the IV line to the neonate. The securement device 10, in addition or in the alternative, can be attached to a fitting attached to the catheter hub or to the IV line 14 itself.

The following discussion of an exemplary method of use will be with reference to FIG. 1, and in the context of intravenous catheterization on the dorsal side of a neonate's hand. As the following discussion with other exemplary uses will illustrate, it is understood that the securement device 10 can also be used with other types of medical line (e.g., tubes, catheters, electrical leads) as well. The discussion of the methods of use is intended to augment the above description of the invention, and, thus, should be read together. The descriptions below applies to both trimmable and non-trimmable patches, except as otherwise noted. However, reference numbers corresponding to the oval patch of FIG. 2 will be used for convenience throughout.

A healthcare provider typically begins the catheterization process by positioning the catheter 16 at a desired location above a vein. The healthcare provider introduces a needle or other stylus through a cannula portion of the medical line 12 and into the skin of the neonate at a desired angle of incidence. For intravenous use, the medical line 12 commonly has an incidence angle of approximately 5 degrees. The healthcare provider then inserts the cannula of the medical line 12 into the neonate and withdraws the needle or stylus. The medical line hub 18 remains exposed above the skin and is connected to the IV line 14.

If using a patch 120 which is designed to be trimmed into an appropriate shape before usage, the healthcare provider cuts the non-fastener portion of the patch 120 into the desired shape for attachment to the patient.

The healthcare provider removes the liner 28 which initially covers the adhesive layer 24 of the patch 20, and attaches the patch 20 to the patient's skin proximate to the insertion site of the indwelling catheter 16. Specifically, the healthcare provider positions the patch 20 near the medical line cannula 12 and places the adhesive layer 24 against the neonate's skin to adhere the patch 20 to the neonate. For the application illustrated in FIG. 1, the patch 20 is positioned on the neonate's forearm or wrist, above the catheter insertion site.

Light pressure over the adhesive layer 24 assures good adhesion between the patch 20 and the neonate's skin. Where a hydrocolloid adhesive is used, the healthcare provider continues to press against the patch 20 in order to warm the patch 20 with the healthcare provider's own body heat so as to activate the adhesive layer, as known in the art. The patch 20, due to its flexibility or rigid curvatures, as explained above, conforms to the contours of the topical surface to which the patch 20 adheres. Attachment of the adhesive layer 24 to the neonate's skin thereby exposes the hook fastener element 26 of the patch 20.

The healthcare provider then removes the liner 48 which initially covers the adhesive layer 48 of the medical line attachment section 36 of the coupler 32. Once the liner 28 is removed, the healthcare provider places the adhesive layer 46 against and wraps the medical line attachment section 36 around the medical line 12 (or medical line hub 18) to adhere the coupler 32 to the medical line 12. Light pressure over the adhesive layer 46 ensures good adhesion between the coupler 32 and the medical line 12. In context of use with a hub 18 having a generally cylindrical shape and frusto-conical portion, the medical line attachment section 36 is wrapped around at least a portion of the circumference of the frusto-conical portion of the hub 18.

After the medical line attachment section 36 of the coupler 32 is attached to the medical line hub 18, the healthcare provider attaches the patch attachment section 34 to the patch 20. When used as illustrated in FIG. 1, the healthcare provider places the VELCRO® loop fastener element 44 against the VELCRO® hook fastener element 26. If the medical line attachment section 36 were wrapped around the underside of the catheter hub 18 (i.e., a side proximate to the skin), the other loop fastener element 42 would be attached to the patch 20. Light pressure over the loop fastener element 44 and onto the hook fastener element 26 assures good adhesion between the hook-and-loop fastener portions 26, 44. Use of a hook-and-loop fastener provides for simple and quick releasable attachment of the medical line 12 and to the neonate's skin without requiring precise alignment or positioning of the VELCRO portions 26, 44 or other components of the securement device 10.

Alternatively, the healthcare provider attaches the coupler 32 to the patch 20 before securing the coupler 32 to the medical line 12. This technique minimizes the pressure applied to the neonate and works well when precise positioning and alignment of the coupler 32 on the medical line 12 is not required.

The healthcare provider may then optionally use one of the piece of tape 50, 52 to further secure the medical line 12 at a location near the cannula insertion point. If used, the healthcare provider places the elongated strip of tape 50 generally perpendicular to and over the medical line 12 near the cannula insertion point. Transpore™ tape 52, which is less adhesive than an acrylic adhesive or a latex-based tape, is preferred to inhibit excoriation of the neonate's skin. This tape strip 50 inhibits lateral movement (i.e., side-to-side movement) of the catheter hub 18.

To disengage the medical line 12 from the neonate, the healthcare provider detaches the loop fastener element 44 of the coupler 32 from the hook fastener element 26 of the patch 20. The medical line 12 can then be attended to (e.g., repositioned, replaced, inspected) while the patch 20 remains attached to the neonate's skin. The same coupler 32 can be used to reattach the same medical line 12 to the patch 20, or a different coupler 32 can be used to attach the medical line 12 to the patch 20. In addition, a different coupler 32 can be used to attach a different medical line 12 to the patch 20 in other applications.

By this configuration and method, the securement device 10 provides releasable engagement of the medical line 12 to the neonate without requiring precise alignment or positioning of the components of the securement device 10. So long as the loop fasteners 42, 44 are placed in contact with the hook fastener 26, the patch 20 and the coupler 32 will cooperate to secure the medical line 12 to the neonate. In addition, the component of the securement device 10, which is attached to the medical line, can be separated from (i.e., is independent of) the component which adheres to the patient. The medical line thus can be inspected, repositioned, replaced, or otherwise serviced without removal of the patch 20, thereby sparing the neonate's skin. Application and removal of surgical tape on the neonate thus is also obviated by the securement device 10. Moreover, the basic design of the patch 20 and the coupler 32 provides for a variety of locations at which the patch 20 and the coupler 32 can be used to secure the medical line 12 to the neonate, as appreciated from the following description.

Figure 8:
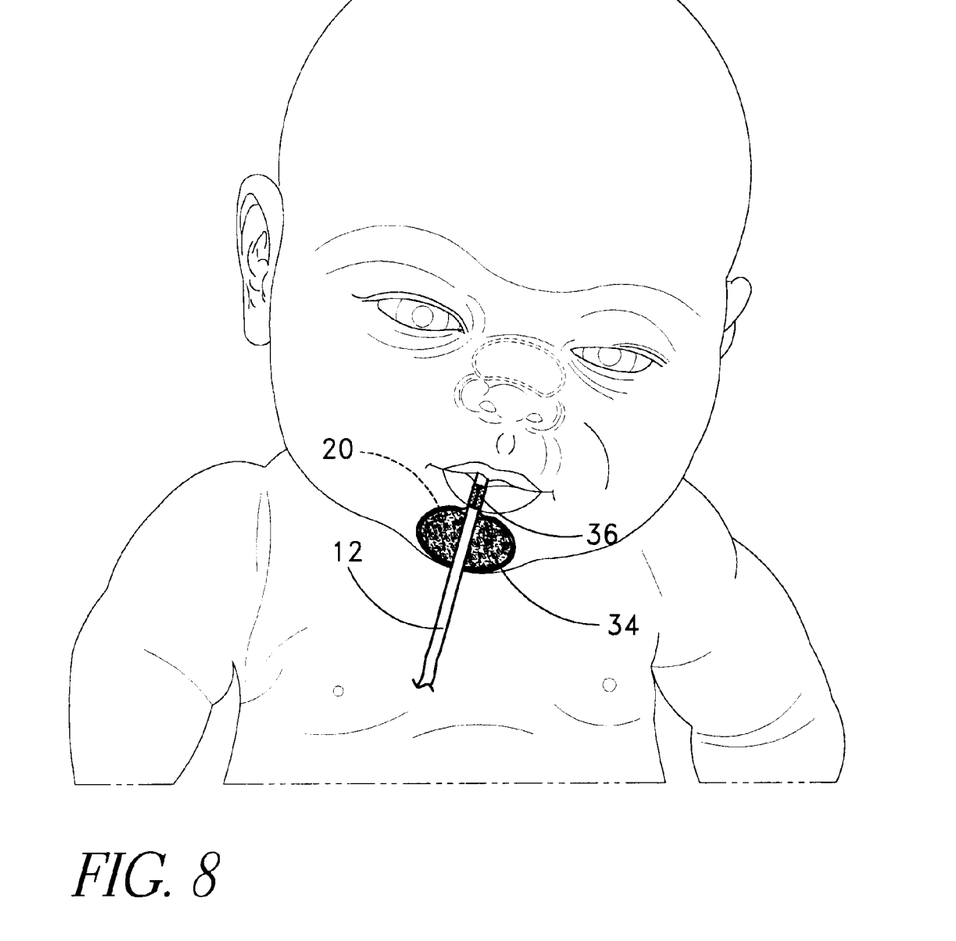
FIG. 8 is a perspective view of the securement device of FIG. 1, illustrating another exemplary use of the device being attached to the neonate's face and securing an endotracheal tube.
Figure 9:
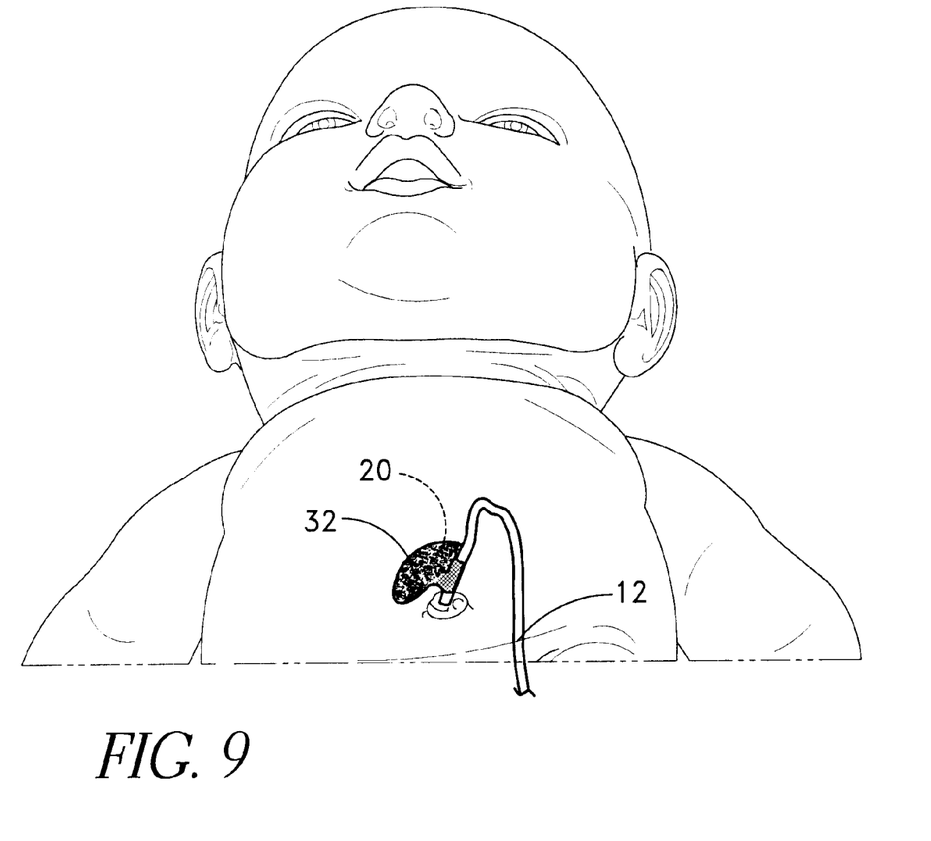
FIG. 9 is a perspective view of the securement device of FIG. 1, illustrating another exemplary use of the device being attached to the neonate's abdomen and securing an umbilical catheter.

FIG. 8 illustrates another exemplary use of the securement device 10, the use being attachment of the securement device 10 to the neonate's face to secure an endotracheal tube 12. The healthcare provider typically begins this attachment process by securing the patch 20 to the neonate's chin in a similar manner as described above. Then, the healthcare provider attaches the coupler 32 to the tube 12 in a similar manner as described above. (Again, the coupler 32 can be attached to the patch 20 before attachment to the endotracheal tube 12.) In this application, the adhesive 46 of the medical line attachment section 36 is positioned to face away from the patient with the medical line attachment section 36 arranged between the neonate's chin/mouth and the endotracheal tube. The healthcare provider presses the loop fastener element 42, which is on a side of the coupler 32 opposite of the adhesive 46, onto the hook fastener element 26 to secure the coupler 32 to the patch 20 in a similar manner as described above.

FIG. 8 also illustrates the general position of the patch 20 on the neonate's nose when used to attach a naso-gastric tube to the neonate. The two securement locations for use with an endotracheal tube and a naso-gastric tube exemplifies a purpose of the double-sided loop fastener elements 42, 44 (and/or the double-sided adhesive 46 on the medical line attachment section 36 in a variation of the illustrated coupler 32, as noted above). If, in the illustrated embodiment, the loop fastener 42 were single-sided, the loop portion 42 would face away from the hook fastener element 26 when the healthcare provider attempted to secure a naso-gastric tube to the neonate's nose (assuming that the loop portion faced the hook portion when the healthcare provider secured the endotracheal tube to the neonate's chin). Thus, the flexible neck 38 must be twisted 180° to allow the hook and loop portions 26, 42 to interengage. However, because the loop fastener elements 42, 44 are double sided, the second loop fastener element 44 on the opposite side can be used to directly attach the coupler 32 to the patch 26 without twisting the flexible neck 38.

Figure 10:
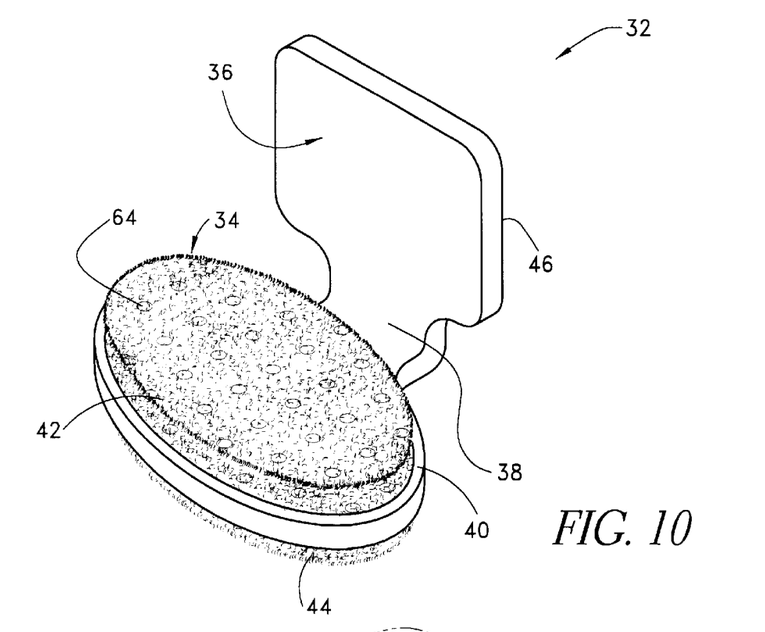
FIG. 10 is an enlarged perspective view of the securement device of FIG. 9 with a coupler of the securement device in bent orientation.

FIGS. 9–11 illustrate another exemplary use of the securement device 10, the use being attachment of the securement device 10 to the neonate's abdomen to secure an indwelling umbilical catheter 12 through the neonate's umbilical stump. The healthcare provider typically begins this attachment process by securing the patch 20 to the neonate's abdomen in a similar manner as described above. Then, the healthcare provider attaches the coupler 32 to the medical line 12 in a similar manner as described above. The healthcare provider then presses the loop fastener element 44 onto the hook fastener element 26 to secure the coupler 32 to the patch 20 in a similar manner as described above.

This application of the securement device 10 illustrates the advantage of the flexible neck 38 on the coupler 32. The flexible neck 38 can be bent so permit the medical line attachment section 36 to assume a different orientation from that of the patch attachment section 34. In the illustrated application, the medical line attachment section 36 lies generally normal to the patch attachment section 34. So oriented, the coupler 32 inhibits migration or dislodgment of the umbilical catheter 12, as well supports at least a portion of the umbilical catheter 12 in a generally upright orientation, the advantages of which are well known in the art.

Although this invention has been described in terms of certain a preferred embodiment and exemplary methods of use, other embodiments and methods of use apparent to those of ordinary skill in the art are also within the scope of this invention. It is also understood that the various modes and variations of the securement device and kit components described above can be used in connection with one another and such variations and modes of the securement device and kit components can be readily adapted by those skilled in the art into a variety of combinations in order to suit one or more particular applications. Accordingly, the scope of the invention is intended to be defined only by the claims that follow.

What is claimed is:

1. A securement device for securing a medical line to the skin of a patient, comprising:
    a patch including at least one fastener element on a first side of the patch and an adhesive on at least a portion of an opposite second side of the patch to secure the patch to the skin of the patient; and
    a coupler having a patch attachment section and a medical line attachment section connected together and both including a front side and an opposite back side, at least two fastener elements, each being cooperative with the fastener element on the patch to releasably secure the coupler to the patch, one being positioned on the front side of the patch attachment section and the other being position on the back side of the patch attachment section, and an adhesive on the front side of the medical line attachment section.

2. A securement device as in claim 1, wherein the fastener elements on the coupler are non-abrasive.

3. A securement device as in claim 2, wherein the fastener elements on the coupler each comprise a plurality of loops, and the fastener element on the patch comprises a plurality of hooks.

4. A securement device as in claim 1, wherein the coupler includes a flexible neck that connects together the patch attachment section and the medical line attachment section.

5. A securement device as in claim 4, wherein the neck comprises a flexible layer of substantially inelastic material.

6. A securement device as in claim 1, wherein the patch is moisture-vapor permeable.

7. A securement device as in claim 6, wherein the patch includes a plurality of perforations and the adhesive is moisture-vapor permeable.

8. A securement device as in claim 1, wherein the adhesive on the patch is hypoallergenic.

9. A securement device as in claim 1, wherein the patch is flexible to conform to a surface profile of the patient's skin.

10. A securement device as in claim 1, wherein the fastener element is sized to cover only a portion of the first side of the patch.

11. A securement device as in claim 10, wherein the patch is configured and sized so that the portion of the patch not covered by the fastener element can be trimmed into a shape appropriate for securing the patch to the skin of the patient.

12. A securement device for securing a medical line to the skin of a patient, comprising:
    a patch including at least one fastener element on a first side of the patch and an adhesive on at least a portion of an opposite second side of the patch to secure the patch to the skin of the patient; and
    a coupler having a patch attachment section, a medical line attachment section connected together by a narrow flexible neck, the patch attachment section including at least one fastener element that is cooperative with the fastener element on the patch to releasably secure the coupler to the patch, and an adhesive on the medical line attachment section.

13. A securement device as in claim 12, wherein the flexible neck has a transverse width that is about one third the transverse width of the patch attachment section.

14. A securement device as in claim 13, wherein the neck comprises a flexible layer of substantially inelastic material.

15. A securement device as in claim 14, wherein the substantially inelastic material has modulus of elasticity of less than about 150,000 psi.

16. A securement device as in claim 14, wherein the flexible layer of material has a tensile strength of at least about 25 lbs./inch.

17. A securement device as in claim 14, wherein the flexible layer of material has a shear strength in a direction perpendicular to an axis of the neck of at least about 0.8 psi.

18. A securement device as in claim 12, wherein the fastener element on the coupler are non-abrasive.

19. A securement device as in claim 18, wherein the fastener element on the coupler comprises a plurality of loops, and the fastener element on the patch comprises a plurality of hooks.

20. A securement device as in claim 19, wherein the patch attachment section includes a front side and an opposite back side, and each of said front and back sides includes a plurality of soft loops that are capable of cooperating with the hooks on the patch.

21. A securement device as in claim 12, wherein the patch is moisture-vapor permeable.

22. A securement device as in claim 21, wherein the patch includes a plurality of perforations and the adhesive is moisture-vapor permeable.

23. A securement device as in claim 12, wherein the adhesive on the patch is hypoallergenic.

24. A securement device as in claim 12, wherein the patch is flexible to conform to a surface profile of the patient's skin.

25. A securement device as in claim 12, wherein the fastener element is sized to cover only a portion of the first side of the patch.

26. A securement device as in claim 25, wherein the patch is configured and sized so that the portion of the patch not covered by the fastener element can be trimmed into a shape appropriate for the region of the patient to which it is applied.

27. A securement device for securing a medical line to the skin of a patient, comprising:
    a patch including a first side and an opposite second side, and an adhesive on at least a portion of the second side of the patch to secure the patch to the skin of the patient;
    a coupler having a patch attachment section and a medical line attachment section being connected together and both including a front side and an opposite back side, and an adhesive on the front side of the medical line attachment section; and
    means for releasably attaching the patch attachment section to the patch regardless of the orientation of the front side of the medical line attachment section relative to the patch.

28. A securement device as in claim 27 additionally comprising means for flexibly connecting the patch attachment section to the medical line attachment section.

29. A securement device as in claim 27, wherein the coupler includes a flexible neck that connects the patch attachment section to the medical line attachment section.

30. A securement device as in claim 29, wherein the patch attachment section and the medical line attachment section each include a base, and a unitary layer of flexible, substantially inelastic material forms the neck and the bases of the patch and medical line attachment sections.

31. A securement device as in claim 27, wherein the patch is flexible.

32. A securement device as in claim 27, wherein the medical line attachment section of the coupler is flexible.

33. A securement device as in claim 27, wherein the patch includes means of permitting moisture-vapor to permeate through the second and first sides of the patch.

34. A securement device as in claim 27, wherein the fastener element is sized to cover only a portion of the first side of the patch.

35. A securement device as in claim 34, wherein the patch is configured and sized so that the portion of the patch not covered by the fastener element can be trimmed into a shape appropriate for the region of the patient to which it is applied.

36. A securement device for securing a medical line to the skin of a patient, comprising:
    a patch including at least one fastener element on a first side of the patch and an adhesive on at least a portion of an opposite second side of the patch to secure the patch to the skin of the patient; and
    a coupler having a patch attachment section and a medical line attachment section connected together and both including a front side and an opposite back side, at least one fastener element being disposed on the front side of the patch attachment section and being cooperative with the fastener element on the patch to releasably secure the coupler to the patch, and at least two adhesive portions, one being disposed on the front side of the medical line attachment section and the other being disposed on the back side of the medical line attachment section.

37. A securement device as in claim 36, wherein the coupler includes another fastener element disposed on the back side of the patch attachment section.

38. A securement device as in claim 36, wherein the fastener element on the coupler comprises a plurality of loops, and the fastener element on the patch comprises a plurality of hooks.

39. A securement device as in claim 36, wherein the coupler includes a flexible neck that connects together the patch attachment section and the medical line attachment section.

40. A securement device as in claim 39, wherein the neck comprises a flexible layer of substantially inelastic material.

41. A securement device as in claim 36, wherein the patch is moisture-vapor permeable.

42. A securement device as in claim 36, wherein the fastener element is sized to cover only a portion of the first side of the patch.

43. A securement device as in claim 42, wherein the patch is configured and sized so that the portion of the patch not covered by the fastener element can be trimmed into a shape appropriate for the region of the patient to which it is applied.

44. A kit having a plurality of parts for securing a medical line to the skin of a neonate, comprising:
    a securement device including,
        a patch including at least one fastener element on a first side of the patch and an adhesive on at least a portion of an opposite second side of the patch to secure the patch to the skin of the patient, and
        a coupler having a patch attachment section and a medical line attachment section connected together and both including a front side and an opposite back side, at least two fastener elements, each being cooperative with the fastener element on the patch to releasably secure the coupler to the patch, one being positioned on the front side of the patch attachment section and the other being position on the back side of the patch attachment section, and an adhesive on the front side of the medical line attachment section; and
    at least one tape strip.

45. A kit as in claim 44 additionally comprising a second patch, one of the patches including a hypoallergenic adhesive.

46. A kit as in claim 44 additionally comprising an additional patch, one of the patches including a fastener element that is sized to cover only a portion of the first side of the patch.

47. A kit as in claim 44 additionally comprising an additional patch that is configured and sized so it can be trimmed into a shape appropriate for the region of the patient to which it is applied by a healthcare practitioner.

48. A kit as in claim 44 additionally comprising a second tape strip, and one of the tape strips having a hypoallergenic adhesive layer.

* * * * *